United States Patent [19]

Shansky et al.

[11] Patent Number: 4,832,947
[45] Date of Patent: May 23, 1989

[54] PROCESS OF INCORPORATING ESSENTIAL OILS INTO HAIR FIBERS AND PERMANENT WAVING PROCESS AND COMPOSITIONS THEREFOR

[75] Inventors: Albert Shansky, Norwalk, Conn.; Prakash C. Purohit, Minneapolis, Minn.

[73] Assignee: A-Veda Corporation, Minneapolis, Minn.

[21] Appl. No.: 256,180

[22] Filed: Oct. 11, 1988

Related U.S. Application Data

[63] Continuation of Ser. No. 31,025, Mar. 27, 1987, abandoned.

[51] Int. Cl.$^4$ ................................................. A61K 7/09
[52] U.S. Cl. ........................................ 424/71; 8/107; 8/111; 8/127.51; 8/406; 123/204; 424/62; 424/70; 424/72
[58] Field of Search .................... 132/7; 8/127.51, 107, 8/111, 406; 424/70, 71, 72, 62

[56] References Cited

U.S. PATENT DOCUMENTS

| | | | |
|---|---|---|---|
| 3,864,476 | 2/1975 | Altien | 424/71 |
| 3,964,499 | 6/1976 | Wajaroff et al. | 132/7 |
| 4,219,449 | 8/1980 | Lenselink et al. | 558/430 |
| 4,622,221 | 11/1986 | Schleppnik et al. | 424/76.4 |
| 4,660,580 | 4/1987 | Hoch et al. | 132/7 |

OTHER PUBLICATIONS

Derwent, (WPI) Acc. No. 74–18911v/10, Abstract of SU 374085, (6/1973).
Derwent, (WPI) Acc. No. 73–59094u/40, Abs. of JP 48048648, (1973).
Derwent, (WPI) Acc. No. 83–843474/50, Abs. of SU 997681, (2/1983).
Derwent, (WPI) Acc. No. 83–63393k/26, Abs. of SU 952257, (8/1982).
Derwent, (WPI) Acc. No. 84–172131/28, Abs. of DE 3346213, (7/1984).
Derwent, (WPI) Acc. No. 87–084841/12, Abs. of SU 1247011, (7/1986).
Websters 3rd New International Dictionary, unbridged, p. 1279.
Hackh's Chemical Dictionary, 4th Ed., McGraw-Hill 1969, pp. 414, 498.

Primary Examiner—A. Lionel Clingman
Assistant Examiner—Linda D. Skaling
Attorney, Agent, or Firm—Peterson, Wicks, Nemer & Kamrath

[57] ABSTRACT

A permanent waving process is disclosed in which an essential oil is incorporated into hair fibers. The incorporated of the essential oil into the hair fiber not only provides capacity to remove bad odors resulting from freshly permanent waved hair but also gives to the hair a supple and smooth feeling. The essential oil is incorporated in the oxidizing or neutralizing solution of the permanent waving process. The essential oils employed are those containing at least one component, ingredient or constituent having an ethylenically unsaturated bond, i.e.

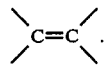

15 Claims, No Drawings

PROCESS OF INCORPORATING ESSENTIAL OILS INTO HAIR FIBERS AND PERMANENT WAVING PROCESS AND COMPOSITIONS THEREFOR

This is a continuation of co-pending application Ser. No. 07/031,025 filed on 3/27/87 now abandoned.

BACKGROUND OF THE INVENTION

1. Field of the Invention

This invention relates to a permanent waving process in which essential oils are incorporated into hair fibers. The incorporation of the essential oils into the hair fibers not only provides capacity to remove bad odors resulting from freshly permanent waved hair, but also imparts a supple and smooth feeling to the hair when the essential oils are incorporated in the oxidizing solution of the permanent waving process. The essential oils employed are those containing at least one compound, constituent or ingredient in the oil having an ethylenically unsaturated double bond.

2. Description of Prior Art

Cold waving or permanent waving of human hair has been knwon for some time. In salons, heat is sometimes applied. The usual procedure involves, in its simplest terms, the application of a hair waving solution or lotion to the hair which softens the hair and allows for reshaping the hair. Subsequently, the hair is set into the new shape or configuration by application of a neutralizing agent.

Thus, in a conventional permanent waving process, the hair is first softened by application of a waving solution which includes a chemical reducing agent. The reducing agent, employed almost universally in cold waving solutions for human hair, is the mercaptan thioglycollic acid, which is used in the form of its ammonium salt, namely, ammonium thioglycolate. Other mercaptans can be used however, as can certain members of the class of compounds known as sulfites. It is a generally accepted theory in the hair waving field that the reducing agent softens the hair by breaking down the disulfide bonds of the hair keratin which is the basic constituent of the hair. The specific linkage which is broken is the cystine linkage, and the breakage of each linkage produces two sulfhydryl groups. After the usual intermediate rinse, the softened hair is placed in a waved configuration, and then rehardened so that it is returned to its original resilient condition and so that it also retains the new wave. The hardening step, also usually referred to as a "neutralization" step, conventionally involves rebuilding a good portion of the broken disulfide bonds, and ordinarily solutions of hydrogen peroxide or alkaline perborates or bromates are employed for this purpose. A considerable number of processes and materials useful in these processes are known for the waving or straightening of hair.

Essential oils have been employed in the past for the purpose of providing a pleasant odor to shampoos, hair tonics and hair grooming or dressing compositions. Essential oils are generally volatile materials produced from odorous plant materials, but can also be synthetically produced.

More specifically, in U.S. Pat. No. 4,460,488, granted on July 17, 1984 to Grollier et al. for "PLANT EXTRACTION RESIDUE AS A THICKENING OR OPACIFYING AGENT FOR A COSMETIC COMPOSITION," a plant extraction residue, remaining after extraction of essential oils therefrom, has been employed as a thickening or opacifying composition for a cosmetic composition, such as creams, gels, make-up, skin masks, hair dyeing or bleaching products, permanents, uncurling products and hair rinse products to be applied before or after hair treatment or blow-dry lotions.

U.S. Pat. No. 4,532,950, granted on Aug. 6, 1985 to Lang et al for "PROCESS FOR THE PERMANENT DEFORMATION OF HAIR," describes a process for permanent deformation of hair, as its title indicates, and is more specifically concerned with a process in which the hair keratin reducing composition or permanent waving solution employed in the first step contains an organic compound having an activated carbon-carbon bond. Illustrative of such compounds are acids, salts thereof, esters, amides and nitriles. The solution may also contain a perfume oil.

SUMMARY OF THE INVENTION

We have ascertained that the incorporation of certain essential oils into the hair fibers by use of oxidizing or neutralizing solutions (also referred to as hardening or setting solutions) eliminates or minimizes any undesirable odor or malodor, and at the same time provides a supple and smooth feel to the hair. Thus, in the process of waving hair comprising the steps of treating the hair with a reducing composition followed by treating of the hair with a neutralizing or oxidizing solution, improvement is obtained by employing a neutralizer or oxidizing solution which contains an essential oil having as at least one component or ingredient thereof, an organic compound containing an ethylenically unsaturated double bond, i.e.

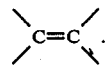

There is also provided by the present invention an improved neutralizing solution or composition containing the desired essential oil as described above.

Accordingly, the present invention is directed to a process for shaping human hair comprising the steps of:

(a) applying to the hair a reducing composition for affecting the configuration of the hair and permitting such reducing composition to act on the hair, and (b) thereafter applying a neutralizer oxidizing composition to set the hair, the improvement wherein said neutralizer oxidizing composition contains the essential oil containing at least one ingredient, component or constituent having an ethylenically unsaturated bond.

The invention also is directed to a neutralizer oxidizing composition for setting the hair after the hair has been treated with a reducing composition, wherein said neutralizer composition is an aqueous solution of an oxidizing agent and contains an essential oil containing at least one constituent having an ethylenically unsaturated bond.

DETAILED DESCRIPTION AND PREFERRED EMBODIMENTS

As indicated in the summary above the present invention lies in having ascertained that an essential oil containing at least one ingredient or constituent having at least one ethylenically unsaturated bond, when used in the neutralizer oxidizing composition, provides not only a desirable odor or fragrance, but also provides a supple and smooth hair feel.

In the treatment of hair for affecting the configuration thereof, i.e. for permanent waving, the hair is first treated with a waving composition which permits the hair to be shaped to a new configuration which new configuration is subsequently fixed by application of a neutralizer or setting composition.

In the first step, the waving solution is a reducing solution and the reduction process is believed to involve the severance of the cystine bonds of the keratin molecule. A preferred reducing agent is ammonium thioglycolate which produces open linkages of cysteine in the hair which may be illustrated by means of the following equation:

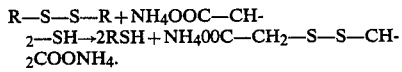

The second step in the process involves the use of an oxidizing agent, such has hydrogen peroxide or a sodium bromate, to reunite the open cysteine into cystine. This may be illustrated by means of the following equation wherein hydrogen peroxide is employed as the oxidizing agent:

The waving or shaping of the hair to a new configuration is accomplished by winding the hair around conventional rods or mandrels, before treatment with the neutralizing oxidizing solution, so that the reuniting of the cysteine into the new position or configuration is achieved.

While the foregoing process is very effective in causing curl formation to take place, it has the very serious drawback of leaving the hair with an adverse malodor. In addition, due to the reduction process which is carried out under highly alkaline conditions (pH 9.22 to 9.6), the hair assumes a porous condition. This results in hair which is rough and brittle, requiring the use of emollients to overcome this poor state.

In the present invention it has been determined that certain essential oils commonly used in aromatherapy have the capacity to remove bad odors from freshly permanent waved hair, and also give the hair a supple and smooth feeling when these essential oils are incorporated in the oxidizing solution of the permanent waving process. It is believed, but we do not wish to be bound thereto, that the essential oils or ethylenically unsaturated constituents thereof react with the open cysteine and is attached to the hair molecule by a coordinate covalent linkage. In order to react with the open linkage of the cysteine, it is necessary that the essential oil contain at least one component or ingredient possessing an ethylenic double bond.

Other than the presence of the essential oil or ingredient thereof containing the ethylenically unsaturated double bond, the neutralizer solution is of a conventional composition, generally an aqueous solution of an oxidizing agent at a pH below 7, generally in the range of about 3.5 to 6.5. Preferred conventional oxidizing agents are hydrogen peroxide, alkaline perborates or bromates. Hydrogen peroxide or alkaline metal bromates are preferred. The neutralizer solutions optionally may also contain opacifier compositions, such as disclosed in our commonly assigned, copending application Ser. No. 892,130, filed July 31, 1986 for "OPACIFYING COMPOSITION AND HAIR TREATING COMPOSITION WITH PROCESS OF USING SAME."

The essential oil may also be incorporated into the reducing composition, although in such composition the use of the essential oil therein is generally for its aromatherapy properties. The usual and well recognized reducing compositions are those containing a mercaptan, such as thioglylcollic acid, generally employed as the ammonium salt, i.e. ammonium thioglycolate. Another mercaptan compound such as monoethanolamine thioglycolate, and various sulfite compositions are also commonly employed. An example of a permanent wave lotion which also contains an opacifier composition is set forth in our copending application noted above.

Essential oils are generally volatile materials produced from odorous plant material, although today many essential oils are synthetically produced. The synthetically produced essential oils may be employed in this invention, as well as those derived directly from plant sources, so long as they contain the necessary ethylenically unsaturated linkage. Generally, these essential oils will contain, as the unsaturated linkage components or constituents, various unsaturated hydrocarbons, aldehydes, ketones and alcohols. The presence of the desirable double bond unsaturation may be determined by standard potassium permanganate titration, commonly employed in analytical chemistry to determine the presence of the ethylenic double bond. A good discussion of essential oils, their composition and production, can be found in Kirk-Othmer Encyclopedia of Chemical Technology, Third Edition, Volume 16, pages 307-329, Copyright 1981, John Wiley & Sons, Inc., the disclosure of which is herein incorporated by reference.

The preferred essential oils useful in this invention, as they contain significant amounts of ethylenically unsaturated compounds and possess desirable aromatherapy properties, are ylang ylang oil, geranium oil, lavender oil and melissa oil. The chief constituents of geranium oil are geraniol and citronellol. Geraniol is also found in lavender oil, although the principal ingredient in lavender oil is ocimene, 2,6-dimethyl-2, 5,7-octa triene, which contains multiple unsaturated double bonds. Geraniol and citronellol are also found in melissa oil along with linalool. Ylang ylang oil also contains geraniol and linalool, and is the most preferred oil of the group.

As can be seen from the foregoing, essential oils having large amounts of double bond unsaturated constituents possessing from about 5-20 carbon atoms are satisfactory for use in the present invention. These may be an unsaturated hydrocarbon (aliphatic, cycloaliphatic or aromatic compounds), alcohols, ketones and aldehydes. As also can be seen from the foregoing, the preferred oils contain relatively large amounts of constituents such as geraniol, citronellol, linalool and ocimene. Accordingly essential oils containing these constituents are more desirable.

The essential oil is employed in an amount by weight of the neutralizing solution of from about 0.1 to 2%. It is generally not necessary to employ more than about 1% which provides the desirable odor control and sufficient amount of ethylenic unsaturation to provide the necessary attachment to the hair fibers. If oils other than the preferred ones noted above are employed, the amount may vary, however, dependent upon the amount of unsaturation present in the particular oil employed.

The emulsion containing the essential oil is prepared by heating the water to about 50° C. and adding the other ingredients (oil phase) also at 50° C. to the water phase and maintaining the temperature at 50° C. while vigorously mixing.

The following examples will serve to illustrate the present invention in which all parts and percentages are by weight unless otherwise specified. Four formulations of oxidizing neutralizing solutions or lotions are set forth in the examples below. Application of these neutralizing formulas subsequent to the treatment with conventional reducing permanent waving solutions or lotions, or those described in our copending application noted earlier, will leave the hair in a supple and smooth feel with no adverse odor being noticeable.

The most preferred formula from the standpoint of odor and overall properties is the following:

EXAMPLE I

| Ingredient | % |
| --- | --- |
| Water | 83.485 |
| Glycerin | 3.000 |
| Hydrogen peroxide (35% solution) | 7.500 |
| Phosphoric acid (85% concentration) | 0.015 |
| Polyoxysorbitan monolaurate | 5.000 |
| Ylang ylang oil | 1.000 | pH = 3.79

Three additional formulas that have proved satisfactory are:

EXAMPLE II

| Ingredient | % |
| --- | --- |
| Water | 79.00 |
| Glycerin | 3.00 |
| Sodium bromate | 12.00 |
| Polyoxysorbitan monolaurate | 5.00 |
| Ylang ylang oil | 1.00 | pH = 6.5

EXAMPLE III

| Ingredient | % |
| --- | --- |
| Water | 83.485 |
| Glycerin | 3.000 |
| Hydrogen peroxide (35% solution) | 7.500 |
| Phosphoric acid (85% concentration) | 0.015 |
| Polyoxysorbitan monolaurate | 5.000 |
| Oil of melissa | 1.000 | pH = 3.79

Example IV

| Ingredient | % |
| --- | --- |
| Water | 83.485 |
| Glycerin | 3.0 |
| Hydrogen peroxide (35% solution) | 7.5 |
| Phosphoric acid (85% concentration) | 0.015 |
| Polyoxysorbitan monolaurate | 5.0 |

| Ingredient | % |
| --- | --- |
| Lavender oil | 1.0 | pH = 3.79

What is claimed is:

1. In a process for shaping or affecting the configuration of hair comprising the steps of:
   (a) applying to the hair a waving composition and permitting said waving composition to act on the hair, and
   (b) thereafter applying a neutralizer composition to set the hair, the improvement wherein said neutralizing composition is an aqueous composition which contains an effective amount of an oxidizing agent and an essential oil having at least one constituent thereof possessing an ethylenically unsaturated bond, said essential oil being present in an amount of about 0.1 to 2% by weight of said neutralizing composition, said essential oil being selected from the group consisting of ylang ylang oil, lavender oil, geranium oil and melissa oil and said constituents thereof possessing an unsaturated bond being selected from the group consisting of geraniol, citronellol, linalool and ocimene.

2. A process as defined in claim 1 wherein said essential oil is ylang ylang oil.

3. A process as defined in claim 1 wherein said neutralizing composition is an aqueous solution of an oxidizing agent and said essential oil is present in an amount of about 1% by weight of said neutralizing composition.

4. A process as defined in claim 3 wherein said oxidizing agent is selected from the group consisting of hydrogen peroxide, alkaline perborates and bromates.

5. A process as defined in claim 4 wherein said oxidizing agent is sodium bromate and said essential oil is ylang ylang oil.

6. A process as defined in claim 4 wherein said oxidizing agent is hydrogen peroxide and said essential oil is ylang ylang oil.

7. A process as defined in claim 1 wherein said waving composition further contains an effective amount of a reducing agent sufficient to sever the cysteine bonds of the keratin molecule of the hair to provide open linkage of cysteine in the hair, and wherein said constituent of said essential oil containing said ethylenically unsaturated bond reacts with said open cysteine linkage and attaches to said keratin molecule of the hair.

8. A process as defined in claim 1 in which said neutralizing solution comprises by weight:

| Ingredient | % |
| --- | --- |
| Water | 83.485 |
| Glycerin | 3.000 |
| Hydrogen peroxide (35% solution) | 7.500 |
| Phosphoric acid (85% concentration) | 0.015 |
| Polyoxysorbitan monolaurate | 5.000 |
| Ylang ylang oil | 1.000 |

9. A process as defined in claim 1 in which said neutralizing solution comprises by weight:

| Ingredient | % |
| --- | --- |
| Water | 79.00 |
| Glycerin | 3.00 |

-continued

| Ingredient | % |
| --- | --- |
| Sodium bromate | 12.00 |
| Polyoxysorbitan monolaurate | 5.00 |
| Ylang ylang oil | 1.00 |

10. A process as defined in claim 1 in which said neutralizing solution comprises by weight:

| Ingredient | % |
| --- | --- |
| Water | 83.485 |
| Glycerin | 3.000 |
| Hydrogen peroxide (35% solution) | 7.500 |
| Phosphoric acid (85% concentration) | 0.015 |
| Polyoxysorbitan monolaurate | 5.000 |
| Oil of melissa | 1.000 |

11. A process as defined in claim 1 in which said neutralizing solution comprises by weight:

| Ingredient | % |
| --- | --- |
| Water | 83.485 |
| Glycerin | 3.000 |
| Hydrogen peroxide (35% solution) | 7.500 |
| Phosphoric acid (85% concentration) | 0.015 |
| Polyoxysorbitan monolaurate | 5.000 |
| Lavender oil | 1.000 |

12. A neutralizing composition for use in a permanent waving process comprising by weight:

| Ingredient | % |
| --- | --- |
| Water | 83.485 |
| Glycerin | 3.000 |
| Hydrogen peroxide (35% solution) | 7.500 |
| Phosphoric acid (85% concentration) | 0.015 |
| Ylang ylang oil | 1.000 |

13. A neutralizing composition for use in a permanent waving process comprising by weight:

| Ingredient | % |
| --- | --- |
| Water | 79.00 |
| Glycerin | 3.00 |
| Sodium bromate | 12.00 |
| Polyoxysorbitan monolaurate | 5.00 |
| Ylang ylang oil | 1.00 |

14. A neutralizing composition for use in a permanent waving process comprising by weight:

| Ingredient | % |
| --- | --- |
| Water | 83.485 |
| Glycerin | 3.000 |
| Hydrogen peroxide (35% solution) | 7.500 |
| Phosphoric acid (85% concentration) | 0.015 |
| Polyoxysorbitan monolaurate | 5.000 |
| Oil of melissa | 1.000 |

15. A neutralizing composition for use in a permanent waving process comprising by weight:

| Ingredient | % |
| --- | --- |
| Water | 83.485 |
| Glycerin | 3.000 |
| Hydrogen peroxide (35% solution) | 7.500 |
| Phosphoric acid (85% concentration) | 0.015 |
| Polyoxysorbitan monolaurate | 5.000 |
| Lavender oil | 1.000 |

* * * * *